(12) United States Patent
Smith et al.

(10) Patent No.: US 7,091,683 B1
(45) Date of Patent: Aug. 15, 2006

(54) METHOD OF MONITORING AND CONTROLLING THE SEATING OF SCREWS TO THE OPTIMUM POINT OF GRIP INDEPENDENT OF SCREW SIZE AND MATERIAL DENSITY

(75) Inventors: Mark Smith, Yardley, PA (US); Joseph Whyte, Branchburg, NJ (US)

(73) Assignee: Intelligent Automation Design, LLC, Yardley, PA (US)

( * ) Notice: Subject to any disclaimer, the term of this patent is extended or adjusted under 35 U.S.C. 154(b) by 0 days.

(21) Appl. No.: 10/970,682

(22) Filed: Oct. 22, 2004

Related U.S. Application Data

(66) Substitute for application No. 60/513,544, filed on Oct. 24, 2003.

(51) Int. Cl.
*H02P 7/00* (2006.01)

(52) U.S. Cl. .................. 318/432; 318/430; 318/434; 318/284; 73/761; 173/176

(58) Field of Classification Search ........ 318/430–434, 318/272, 599, 283, 284; 173/176, 217; 388/804, 388/811; 700/168; 73/761
See application file for complete search history.

(56) References Cited

U.S. PATENT DOCUMENTS

| | | | |
|---|---|---|---|
| 4,283,830 A | | 8/1981 | Gallizio et al. |
| 4,426,887 A | | 1/1984 | Reinholm et al. |
| 4,450,727 A | | 5/1984 | Reinholm et al. |
| 4,906,980 A | * | 3/1990 | Fukuhara .................. 340/680 |
| 4,995,094 A | * | 2/1991 | Aio ............................ 388/840 |
| 5,061,885 A | * | 10/1991 | Fukuhara .................. 318/434 |
| 5,404,643 A | * | 4/1995 | Rice ......................... 29/898.09 |
| 5,440,215 A | * | 8/1995 | Gilmore ..................... 318/432 |
| 5,493,913 A | | 2/1996 | Layer et al. |
| 5,538,423 A | | 7/1996 | Coss et al. |
| 5,563,482 A | * | 10/1996 | Shaw et al. ................ 318/272 |
| 5,591,919 A | * | 1/1997 | Hathaway et al. ............ 73/761 |
| 5,637,968 A | * | 6/1997 | Kainec et al. ............... 318/432 |

(Continued)

FOREIGN PATENT DOCUMENTS

CN 1101580 A 4/1995

*Primary Examiner*—Paul Ip
(74) *Attorney, Agent, or Firm*—Blank Rome LLP

(57) ABSTRACT

A method of controlling a motor (106) used to drive a screwdriver bit (105) such that screws (107) are seated to the optimum point of grip between the screw (107) and the work piece material. An electronic control circuit controls the speed and output torque of the motor (106). The control system utilizes pulse width modulation (PWM) to control motor (106) speed and torque. The PWM signal controls the duty cycle of the transistors that supply current to the motor (106). The amount of current flowing through the motor (106) coils is proportional to the amount of torque the motor (106) is producing. Motor (106) current is measured as voltage produced across a precision resistor that is in series with the motor (106) coils. As the current in the motor (106) increases, the voltage across the resistor increases (V=IR). To accurately measure the torque, as measured by the voltage across the precision resistor, a capacitor with a resistor and/or a diode is used to average the analog signal that is measured by the microprocessor. The microprocessor further filters the analog signal using an averaging formula to produce a stable value corresponding to motor (106) torque/current. When a decrease in current, corresponding to a drop in torque, is detected at the optimum point of grip, the controller (100) stops the motor (106).

8 Claims, 2 Drawing Sheets

U.S. PATENT DOCUMENTS

| | | | |
|---|---|---|---|
| 5,731,673 A * | 3/1998 | Gilmore | 318/432 |
| 5,754,019 A * | 5/1998 | Walz | 318/434 |
| 5,889,922 A * | 3/1999 | Bufe et al. | 388/804 |
| 5,890,405 A | 4/1999 | Becker | |
| 6,084,366 A * | 7/2000 | Koselke et al. | 318/375 |
| 6,424,799 B1 * | 7/2002 | Gilmore | 388/811 |
| 6,479,958 B1 * | 11/2002 | Thompson et al. | 318/430 |
| 6,536,536 B1 | 3/2003 | Gass et al. | |
| 6,553,321 B1 | 4/2003 | Siegel et al. | |
| 6,571,179 B1 | 5/2003 | Siegel | |
| 6,629,055 B1 | 9/2003 | McGee et al. | |
| 6,687,567 B1 * | 2/2004 | Watanabe | 700/168 |
| 6,836,614 B1 * | 12/2004 | Gilmore | 388/811 |
| 2002/0050364 A1 | 5/2002 | Suzuki et al. | |
| 2002/0153856 A1 * | 10/2002 | Gilmore | 318/599 |
| 2003/0037423 A1 | 2/2003 | Siegel | |
| 2003/0065456 A1 | 4/2003 | McGee et al. | |
| 2003/0065474 A1 | 4/2003 | McGee et al. | |
| 2003/0121685 A1 * | 7/2003 | Yamamoto | 173/217 |
| 2003/0149508 A1 * | 8/2003 | Watanabe | 700/168 |
| 2003/0173096 A1 * | 9/2003 | Setton et al. | 173/176 |
| 2004/0217727 A1 * | 11/2004 | Gilmore | 318/599 |

* cited by examiner

METHOD OF MONITORING AND CONTROLLING THE SEATING OF SCREWS TO THE OPTIMUM POINT OF GRIP INDEPENDENT OF SCREW SIZE AND MATERIAL DENSITY

REFERENCE TO RELATED APPLICATION

The present application claims the benefit of U.S. Provisional Patent Application No. 60/513,544, filed Oct. 24, 2003, whose disclosure is hereby incorporated by reference in its entirety into the present disclosure.

FIELD OF THE INVENTION

The present invention is directed to a method of monitoring and controlling the seating of screws and more particularly to such a method which minimizes or avoids stripping.

DESCRIPTION OF RELATED ART

When using screws (107) to fasten two materials together, the objective is to stop turning the screw (107) when the optimum point of grip is achieved between the two materials and the screw (107). The torque required to seat the screw (107) increases as the screw (107) passes through the various zones of the seating process. Once the optimum point of grip is reached, the torque required to continue turning the screw (107) decreases rapidly as the screw (107) enters the strip or material yield zone.

Traditional approaches have used clutches configured with a prefixed torque limit to disengage the motor (106) turning the screwdriver bit (105) once the preset torque value has been reached. There are a number of problems associated with the use of clutches in screw (107) seating. As mechanical devices, clutches wear over time and their accuracy and repeatability suffer as a result. In addition, a device that stops the turning of the screw (107) when a specific torque threshold has been reached does not stop the screws (107) at the optimum point of grip. Torque thresholds do not account for slight variations in screw (107) size and shape as well as slight variations in the density of the material the screw (107) is being driven into. Finally, devices that use torque thresholds as the determining factor have to be specifically configured for each screw (107) and material combination.

To overcome these problems, some patents monitor the various torque zones in the screw (107) seating process and stop the motor (106) when an increase in the rate of change of torque is recognized. This rate of change increase corresponds to the head of the screw (107) coming in contact with the material the screw (107) is being driven into. However, by stopping the screw (107) when a rate of change of increase in torque is recognized, the screw (107) is stopped prior to reaching the optimum point of grip. Others have improved on this approach by moving a fixed distance after the rate of change is recognized. This moves the seating of the screw (107) closer to optimum point of grip but will stop the screw (107) prior to or after the optimum point of grip. None of these approaches eliminates the need to configure the tool for the specific screw (107) and material density being used.

SUMMARY OF THE INVENTION

To avoid the above and other problems, the present invention is directed to a method of seating screws (107) to the optimum point of grip by stopping the motor (106) when a decrease in the rate of change of torque is realized. By averaging torque readings, the controller (100) smoothes the torque rise and falls that occur due to inconsistencies in the material and screw (107). This in turn, eliminates the possibility of a false decrease in the rate of change stopping the motor (106) when it is not fully seated at the optimum point of grip. The speed of the motor (106) is controlled directly by the controller (100). As the screw (107) passes through its various seating zones, this zone change is detected by the controller (100) and the speed of the motor (106) lowered to insure the motor (106) is stopped at the instant the controller (100) detects the optimum point of grip. This method makes the tool completely independent of the screw (107) size, shape and material, eliminating the need to configure the tool.

The control system in one embodiment utilizes pulse width modulation (PWM) to control motor (106) speed and torque. The PWM signal controls the duty cycle of the transistors that supply current to the motor (106). The amount of current flowing through the motor (106) coils is proportional to the amount of torque the motor (106) is producing.

BRIEF DESCRIPTION OF THE DRAWINGS

A preferred embodiment will be set forth with reference to the drawings, in which.

DETAILED DESCRIPTION OF THE PREFERRED EMBODIMENT

Figure 1:
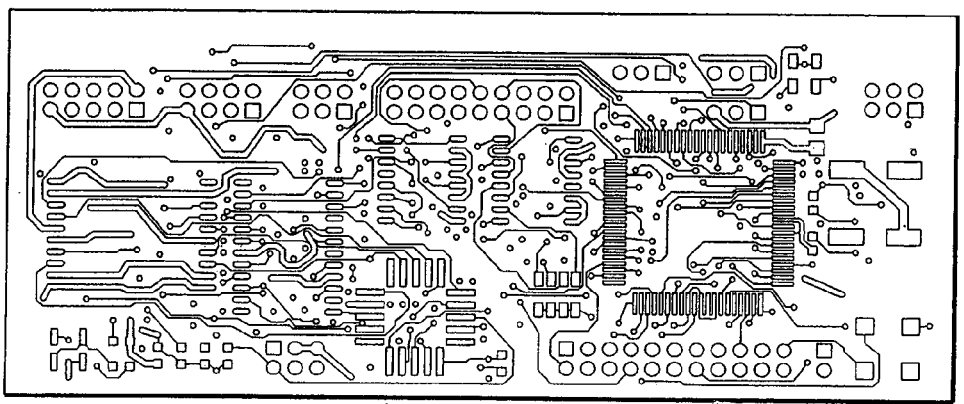
FIG. 1 shows a motor controller.
Figure 2:
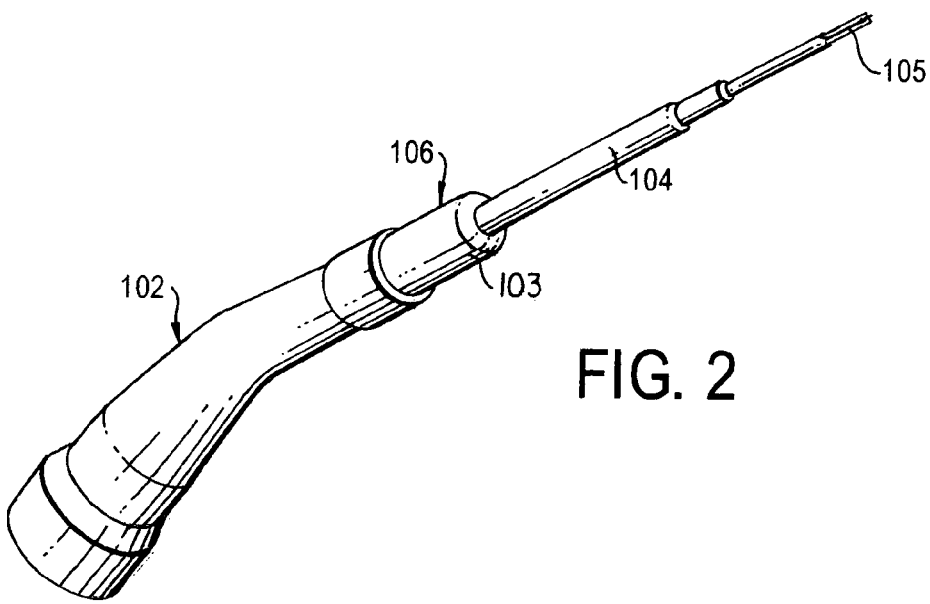
FIG. 2 shows a surgical screwdriver.
Figure 3:
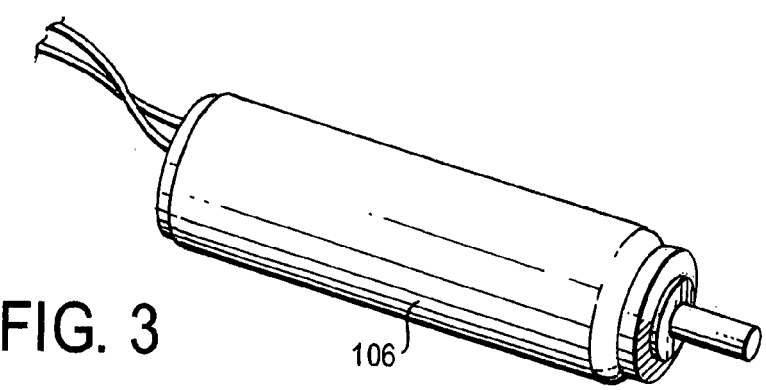
FIG. 3 shows a miniature motor.
Figure 4:
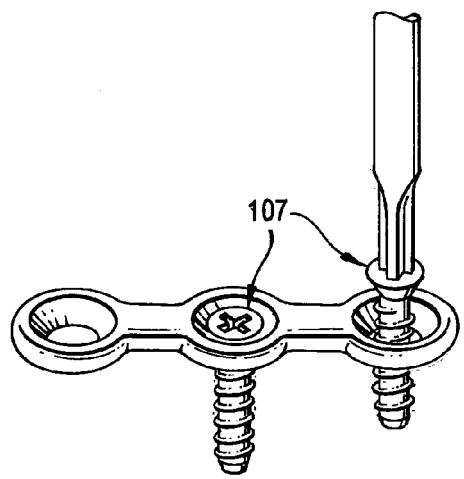
FIG. 4 shows surgical screws.
Figure 5:
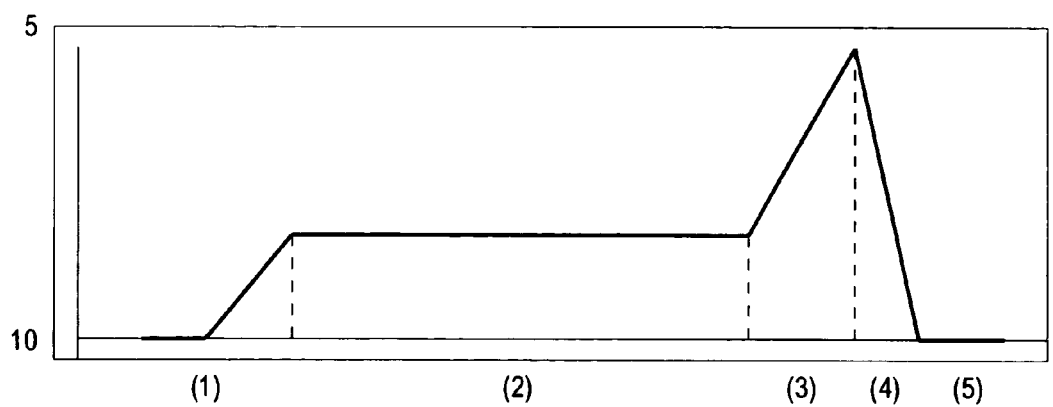
FIG. 5 shows a seating torque profile.

In the preferred embodiment, the torque is controlled in the following manner, which will be explained with reference to FIG. 5. The seating torque profile shown in FIG. 5 can be divided into the following zones.

Zone 1: The screw (107) tip makes contact with the material and the required torque level ramps up until the barrel of the screw (107) is reached.

Zone 2: The barrel of the screw (107), which is of a relatively constant diameter, requires a constant torque to continue driving the screw (107) into the material.

Zone 3: Once the barrel is seated into the material, the torque required to continue driving the screw (107) rises significantly as the head of the screw (107) comes in contact with the material. The required torque to turn the screw (107) continues to rise until the optimum point of grip is reached, which occurs at the transition point from zone 3 to zone 4.

Zone 4: In zone 4, the torque required to continue turning the screw (107) drops significantly as the threads that were created in the material begin to strip. This dramatic decrease in torque continues until the screw (107) completes one full revolution beyond the optimum point of grip.

Zone 5: After one full revolution beyond the optimum point of grip has been completed, all the threads previously created in the material will be stripped. The torque required to continue turning the screw (107) is the same as the torque level before the screw (107) seating process started.

Thus, by measuring the torque, the controller can determine whether the optimum point in the seating torque profile has been reached and can control the motor accordingly.

A motor (106) used to drive a screwdriver bit (105) is controlled such that screws (107) are seated to the optimum point of grip between the screw (107) and the work piece material. An electronic control circuit (108) controls the speed and output torque of the motor (106). The control system utilizes pulse width modulation (PWM) to control motor (106) speed and torque. The PWM signal controls the duty cycle of the transistors that supply current to the motor (106). The amount of current flowing through the motor (106) coils is proportional to the amount of torque the motor (106) is producing. Motor (106) current is measured as voltage produced across a precision resistor that is in series with the motor (106) coils. As the current in the motor (106) increases, the voltage across the resistor increases (V=IR). To accurately measure the torque, as measured by the voltage across the precision resistor, a capacitor with a resistor and/or a diode is used to average the analog signal that is measured by the microprocessor. The microprocessor further filters the analog signal using an averaging formula to produce a stable value corresponding to motor (106) torque/current. When a decrease in current, corresponding to a drop in torque, is detected at the optimum point of grip, the controller (100) stops the motor (106).

Motor (106) current is measured as voltage produced across a precision resistor that is in series with the motor (106) coils. As the current in the motor (106) increases, the voltage across the resistor increases (V=IR). To accurately measure the torque, as measured by the voltage across the precision resistor, a capacitor with a resistor and/or a diode is used to average the analog signal that is measured by the microprocessor. The microprocessor further filters the analog signal using an averaging formula to produce a stable value corresponding to motor (106) torque/current.

Sample averaging formula:

$$(\text{Current value} \times 9.9 + \text{New Value} \times 0.1)/10 = \text{New Current Value}$$

Averaging the analog signal prevents random peaks/spikes and valleys/drops from creating false triggers. Variations to the averaging formula can be used to adjust the weighting applied to the current and new value.

The motor (106) speed is determined by monitoring the frequency of the Hall-effect signals produced as the motor (106) turns. External devices such as an encoder or resolver can also be used as feedback devices. The motor (106) current and speed are measured by the microprocessor, which determines how the motor (106) is controlled using the PWM signal.

While a preferred embodiment has been set forth in detail, it will be appreciated that other embodiments can be realized within the scope of the invention. For example, the invention is not limited to surgical screws, but can instead be applied to any system in which it is desired to prevent stripping. Therefore, the present invention should be construed as limited only by the appended claims.

What is claimed is:

1. A method of controlling a motor (106) used to drive a screwdriver bit (105) such that screws (107) are seated to the optimum point of grip between the screw (107) and the work piece material, the method comprising:
   (a) detecting a torque of the motor;
   (b) determining a time when the torque reaches a maximum by an average means for determining an average value as a function of a current value and a new value, thereby determining the optimum point of grip; and
   (c) stopping the motor at the optimum point of grip.

2. A method according to claim 1, wherein step (b) comprises determining a time when a rate of change of the torque becomes negative.

3. A method according to claim 1, wherein step (a) comprises averaging detected values of the torque over time.

4. A method according to claim 3, wherein step (b) comprises determining a time when a rate of change of the torque becomes negative.

5. A method according to claim 4, further comprising controlling a speed of the motor (106) in accordance with the detected torque.

6. A speed/torque controller (100) for controlling the rotation speed and output torque of the motor (106) with either sensor feedback or back EMF used to monitor motor (106) speed and current used to monitor motor (106) torque, the controller comprising:
   a detector for detecting the output torque of the motor; and
   a control circuit for determining a time when the torque reaches a maximum by an average means for determining an average value as a function of a current value and a new value, thereby determining the optimum point of grip, and stopping the motor at the optimum point of grip.

7. A controller according to claim 6, wherein said control circuit removes power to the motor (106) when the optimum grip threshold is detected.

8. A controller according to claim 7, wherein the control circuit stops the motor (106) by dynamically braking the motor (106).

* * * * *